United States Patent
Cammue et al.

(10) Patent No.: US 12,329,743 B2
(45) Date of Patent: *Jun. 17, 2025

(54) **COMPOSITIONS AGAINST *CANDIDA* INFECTIONS**

(71) Applicants: Katholieke Universiteit Leuven, Leuven (BE); Unviersiteit Antwerpen, Antwerp (BE)

(72) Inventors: Bruno Cammue, Alsemberg (BE); Karin Thevissen, Bierbeek (BE); Kaat De Cremer, Bierbeek (BE); Paul Cos, Oostmalle (BE)

(73) Assignees: Katholieke Universiteit Leuven, Leuven (BE); Universiteit Antwerpen, Antwerp (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,582

(22) Filed: Sep. 13, 2023

(65) Prior Publication Data

US 2023/0414570 A1    Dec. 28, 2023

Related U.S. Application Data

(63) Continuation of application No. 16/631,878, filed as application No. PCT/EP2018/068192 on Jul. 5, 2018, now Pat. No. 11,793,790.

(30) Foreign Application Priority Data

Jul. 18, 2017  (GB) ..................... 1711512
Sep. 20, 2017  (LU) ..................... 100445

(51) Int. Cl.
*A61K 31/4164*  (2006.01)
*A61K 9/00*     (2006.01)
*A61K 9/06*     (2006.01)
*A61K 31/14*    (2006.01)
*A61P 31/10*    (2006.01)

(52) U.S. Cl.
CPC ........ *A61K 31/4164* (2013.01); *A61K 9/0034* (2013.01); *A61K 9/06* (2013.01); *A61K 31/14* (2013.01); *A61P 31/10* (2018.01)

(58) Field of Classification Search
CPC ...... A61K 31/4164; A61K 31/14; A61P 31/10
See application file for complete search history.

(56) References Cited

U.S. PATENT DOCUMENTS

| | | |
|---|---|---|
| 4,091,090 A | 5/1978 | Sipos |
| 4,962,093 A | 10/1990 | Ohkawa et al. |
| 2004/0023960 A1 | 2/2004 | Huskey et al. |
| 2004/0171873 A1 | 9/2004 | Gutman et al. |
| 2007/0053971 A1 | 3/2007 | Dale |
| 2015/0182527 A1* | 7/2015 | Pendleton .......... A61K 31/4196 514/256 |
| 2016/0206523 A1 | 7/2016 | Obias et al. |

FOREIGN PATENT DOCUMENTS

| | | | |
|---|---|---|---|
| EP | 0832649 | * | 1/1998 |
| EP | 0832649 A1 | | 1/1998 |

OTHER PUBLICATIONS

Cleary, et al., "Imidazoles and triazoles in antifungal therapy", Drug Selection Perspectives, vol. 24, pp. 148-152, Feb. 1990.
Ghannoum, et al., "Antifungal Agents: Mode of Action, Mechanisms of Resistance, and Correlation of These Mechanisms with Bacterial Resistance", vol. 12, No. 4, pp. 501-517, 1999.
Portillo, et al., "Mode of action of miconazole on yeasts: inhibition of the mitochondrial ATPase", Eur. J. Biochem., pp. 273-276, 1984.
Swamy, et al., "Studies on the Mechanism of Action of Miconazole: Effect of Miconazole on respiration and Cell Permeability of Candida albicans", Antimicrobial Agents and Chemotherapy, vol. 5, No. 4, pp. 420-425, Apr. 1974.
Trojer, et al., "Imidazole and Triazole Coordination Chemistry for Antifouling Coatings", Hindawi, Journal of Chemistry, pp. 1-24, 2013.
European Patent Office Search Report in reference to co-pending European Patent Application No. PCT/EP2018/068192 filed Jul. 5, 2018.

* cited by examiner

*Primary Examiner* — Marcos L Sznaidman
(74) *Attorney, Agent, or Firm* — Hodgson Russ LLP

(57) ABSTRACT

Provided herein are compositions for topical use comprising an imidazole or a salt thereof, and domiphen bromide as active ingredients for use in treating or preventing a fungal infection, wherein said imidazole is chosen from ketoconazole and clotrimazole as active ingredients for use in treating or preventing a fungal infection.

7 Claims, 11 Drawing Sheets

COMPOSITIONS AGAINST *CANDIDA* INFECTIONS

CROSS-REFERENCE TO RELATED APPLICATIONS

This application is filed as a continuation of U.S. application Ser. No. 16/631,878 filed on Jan. 17, 2020, which is a national stage entry of PCT/EP2018/068192 filed on Jul. 15, 2018, which claims priority to GB application 1711512.2 filed Jul. 18, 2018, and LU application LU100445 filed Sep. 20, 2017, the contents of each of which are incorporated herein by reference in their entireties.

FIELD OF THE INVENTION

The present invention relates pharmaceutical compositions of miconazole and quaternary ammonium salts against *Candida* infections, in particular recurrent vaginal candidiasis.

ABSTRACT

Mucosal biofilm-related fungal infections are very common and the incidence of recurrent oral and vulvovaginal candidiasis is significant.

Various antifungal compounds have been described to combat *Candida* infections. A well-known composition for treatment of vulvovaginal candidiasis comprises miconazole nitrate as active ingredient and its sold under de tradename Gyno Daktarin. The composition comprises polyethylene glycol (PEG-6 and PEG-32) glycol stearate, oleoyl macrogol glycerides, liquid paraffin, butylhydroxyanisole, benzoic acid.

EP0832649 describes an synergistic effect of miconazoles and quaternary ammonium salts on cultures of *Candida albicans*, *Staphylococcus aureus* and a number of *Trichopython* species. US4091090 discloses topical antifungal effect of domiphen bromide. Recurrent infections with *Candida* are increasing and alternative more effective pharmaceutical compositions are desired.

SUMMARY OF THE INVENTION

The present invention identified novel combinations of miconazole (MC) and the quaternary ammonium salt domiphen bromide which is particularly effective against *Candida* sp. and this as well on in vitro cultures as in an experimental setting using a rat model with a vaginal candida infection.

The present invention illustrates that domiphen bromide and miconazole display synergistic antibiofilm activity, based on determination of the fractional inhibitory concentration indices. Using real-time propidium iodide staining, domiphen bromide combined with miconazole , results in the killing of biofilm cells already after 2 h treatment and provides a >3 LOG units reduction of cfu (colony forming units) in the treated biofilms after 24 h.

The invention is summarised in the following statements:
1. A composition for topical use comprising miconazole or a salt thereof and domiphen bromide as active ingredients for use in treating or preventing a fungal infection.
2. The composition according to statement 1, for use in treating or preventing a fungal infection wherein the fungal infection is an infection with *Candida* sp.
3. The composition according to statement 1 or 2, for use in treating or preventing a fungal infection, wherein the fungal infection is an infection with *Candida albicans* or *Candida glabrata*.
4. The composition according to any one of statements 1 to 3, for use in treating a biofilm formed by *Candida* sp.
5. The composition according to any one of statements 1 to 4, for use in treating or preventing a vulvovaginal infection.
6. The composition according to any one of statements 1 to 5, for use in treating or preventing a fungal infection, which is formulated as a cream.
7. The composition according to any one of statements 1 to 6, for use in treating or preventing a fungal infection, further comprising a mucoadhesive.
8. The composition according to any one of statements 1 to 7, for use in treating or preventing a fungal infection, wherein the molar excess of miconazole or a salt over domiphen bromide is between 2 and 4.
9. The composition according to any one of statements 1 to 8, for use in treating or preventing a fungal infection wherein the concentration of miconazole and its salt in said composition is between 2 and 5% (w/w).
10. The composition according to any one of statements 1 to 9, for use in treating or preventing a fungal infection, wherein the molar excess of miconazole or a salt over domiphen bromide is between 2 and 4.
11. The composition according to any one of statements 1 to 10, for use in treating or preventing a fungal infection wherein the concentration of miconazole nitrate is about 2% (w/w) and the molar excess of miconazole nitrate over domiphen bromide is about 3 .
12. The composition according to any one of statements 1 to 11, for use in treating or preventing a fungal infection, wherein the composition is applied over a period of 14 days.
13. A pharmaceutical composition comprising an physiologically acceptable carrier and comprising as active antifungal ingredients a mixture of miconazole or a salt thereof and domiphen bromide.
14. The composition according to statement 13, comprising miconazole nitrate.
15. The composition according to statement 13 or 14, which is a crème with a viscosity of between 300 cp and 300 cp at 180 rmp.
16. The composition according to any one of statements 12 to 15, which has a pH of between 2,7 and 3,5.
17. The composition according to statement any one of statements 12 to 16, wherein the molar excess of miconazole or a salt over domiphen bromide is between 2 and 4.
18. The composition according to any one of statements 12 to 17, wherein the concentration of miconazole and its salt in said composition is between 2 and 5% (w/w).
19. The composition according to any one of statements 12 to 18, further comprising a mucoadhesive.
20. The composition according to any one of statements 12 to 19, which is packaged in an applicator for vaginal delivery.
21. A method treating or preventing a fungal infection comprising the step of administering an effective amount of miconazole or a salt thereof and domiphen bromide.
22. The method according to statement 21, wherein the fungal infection is an infection with *Candida* sp.
23. The method according to statement 21 or 21, wherein the fungal infection is a vulvovaginal infection.

DETAILED DESCRIPTION OF THE INVENTION

BRIEF DESCRIPTIONS OF THE FIGURES

Abbreviation used in the figures are: MCZ: miconazole; DM: domiphen bromide; BKC: benzalkonium chloride; DC: dequalinium bromide; TB; tetraethylammonium bromide; BTC: bezethonium chloride.

FIG. 1. Combined domiphen bromide-miconazole treatment reduces metabolic activity of *C. albicans* biofilm cells. The values represent the mean metabolic activity of 4 independent biological replicates, determined by CTB viability staining.

FIG. 2. Metabolic activity of *C. albicans* biofilm cells after combination treatment of miconazole with quaternary ammonium compounds. The values represent the mean metabolic activity of 4 independent biological replicates, determined by CTB viability staining.

2A: miconazole (MCZ) and benzalkonium chloride (BKC)

2B: miconazole (MCZ) and tetraethylammonium bromide (TB)

2C: miconazole (MCZ) and dequalinium chloride (DC)

FIG. 3. PI fluorescence in *C. albicans* biofilms cells after combination treatment with miconazole and quaternary ammonium compounds. PI fluorescence was measured each 15 minutes during 17 h in *C. albicans* biofilm cells after treatment with miconazole and domiphen bromide, benzalkonium chloride, bezethonium chloride or dequalinium chloride.

3A : miconazole and benzalkonium chloride
3B : miconazole and domiphen bromide
3C : miconazole and bezethonium chloride
3D : miconazole and dequalinium chloride FIG. 4. Survival of *C. albicans* biofilms cells after combination treatment with miconazole and quaternary ammonium compounds. Mean log CFU values ±SD are shown for at least 4 biological replicates. Statistical analysis was performed to assess significant differences between single treatment with either tetraethylammonium bromide (50 µM), bezethonium chloride (50 µM), dequalinium chloride (12.5 µM), benzalkonium chloride (50 µM) and domiphen bromide (50 µM) or combinations with miconazole. A 2-way ANOVA and Sidak's multiple comparisons test was applied and significant P-values are shown.

FIG. 5. Intravaginal fungal burden of all groups at different time points p.i.

The burden is shown as the log of the colony forming units (cfu) present on the vaginal swab. Errors bars represent SEM. G: treatment group.

FIG. 6: Intravaginal fungal burden of all groups.

The burden is shown as the area under the curve (AUC) compared to the control group (G1) (=100%). shown as the log of the colony forming units (cfu) present on the vaginal swab. Errors bars represent SEM. G: treatment group.

Figure 9:
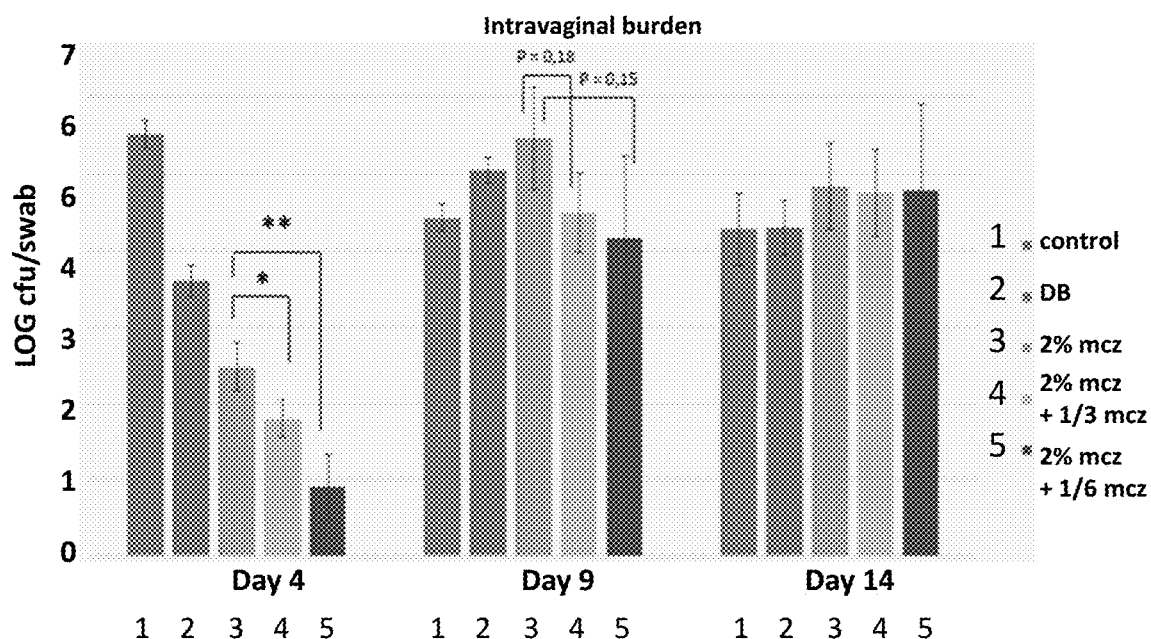

FIG. 9 summarises the result of intravaginal burden of different formulations on day 4, 9 and 14 post infection.

Figure 10:
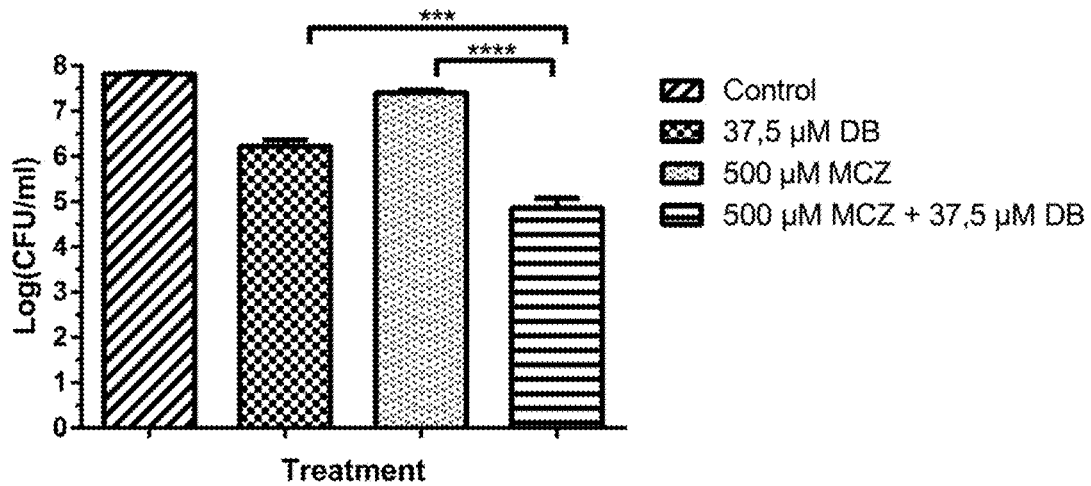

FIG. 10 shows survival of *C. glabrata* biofilm cells after single -or combination treatment with MCZ and DB.

Figure 11:
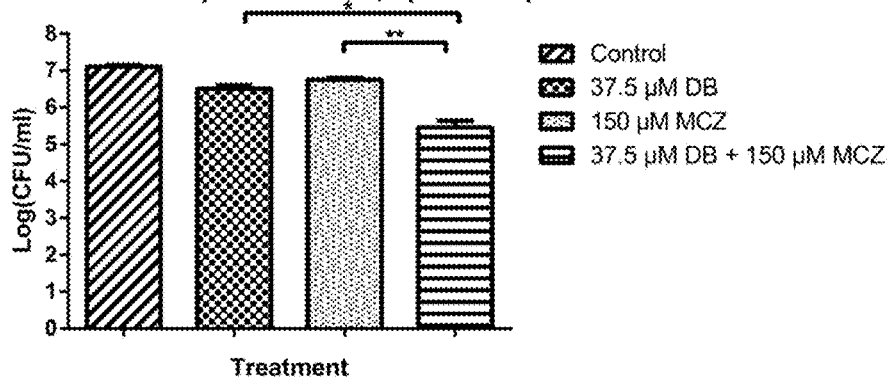
Figure 11:
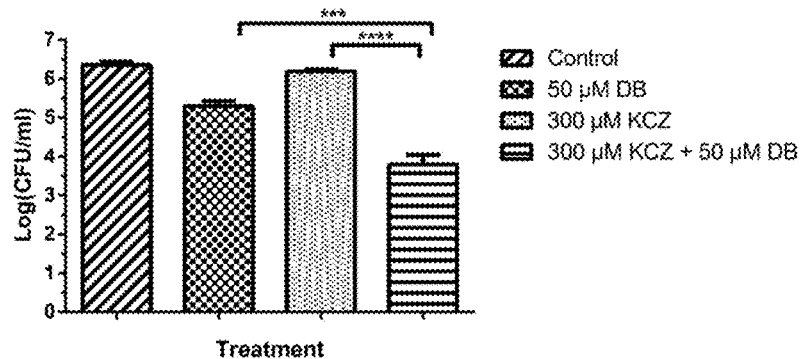
Figure 11:
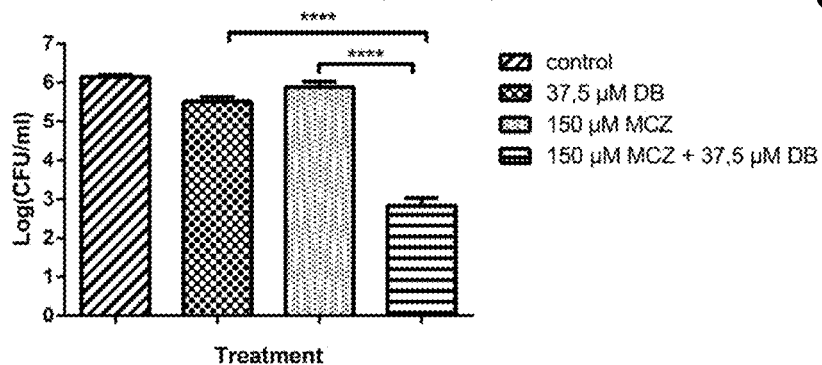
Figure 11:
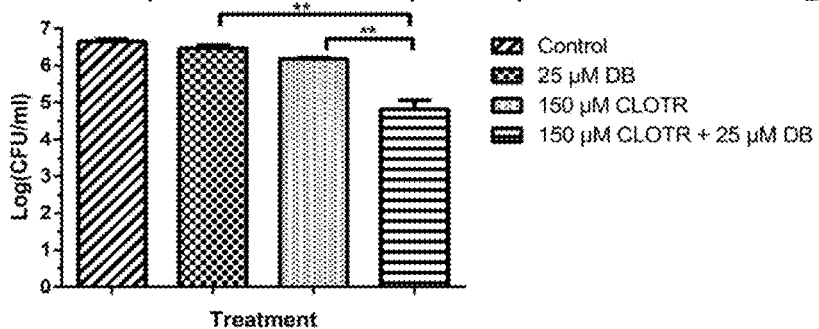
Figure 11:
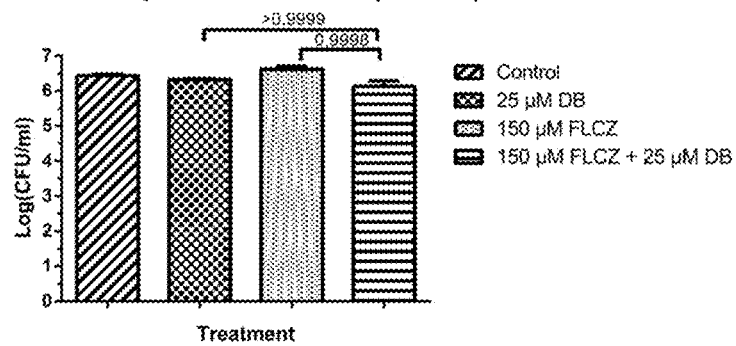
Figure 11:
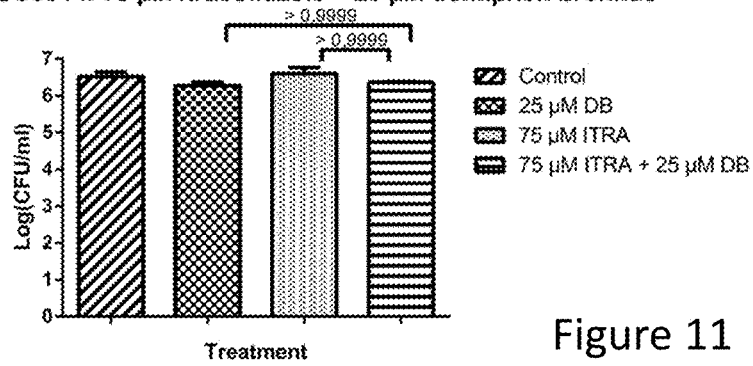
Figure 11:
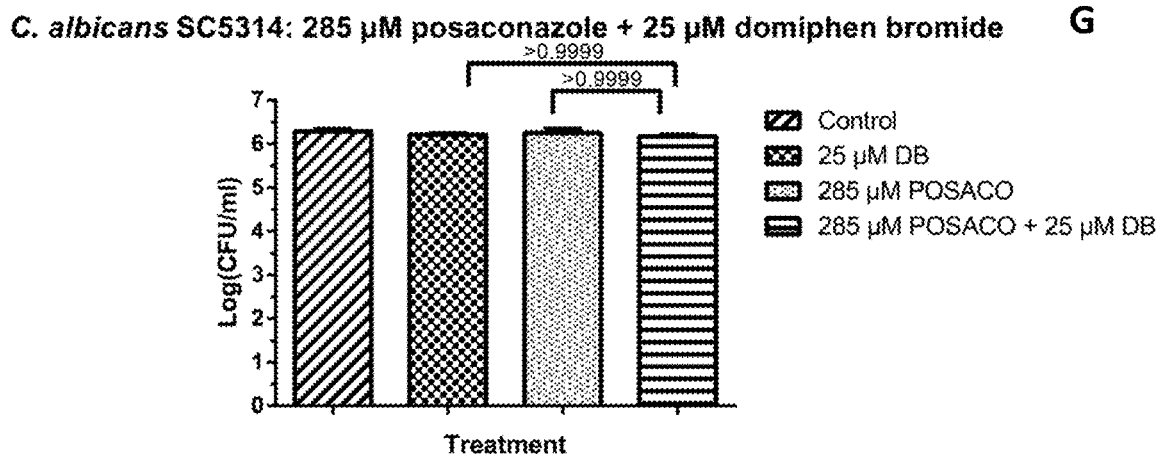

FIG. 11 shows survival of *C. albicans* biofilm cells after single -or combination treatment with an antimycotic and domiphen bromide.

Figure 12:
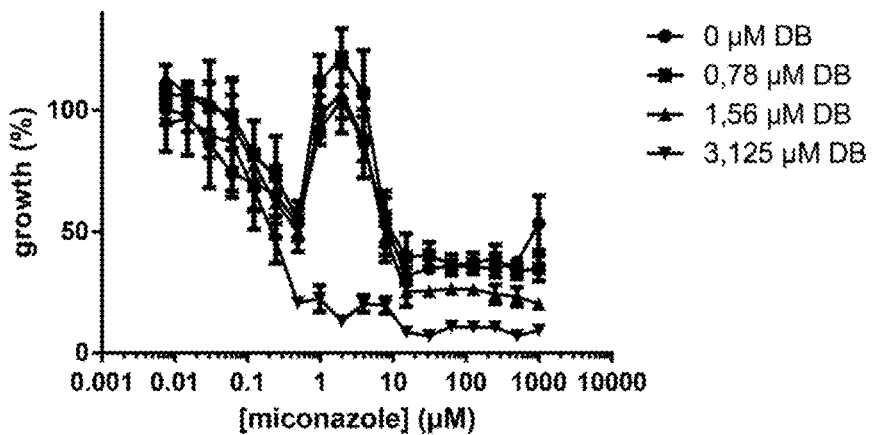
Figure 12:
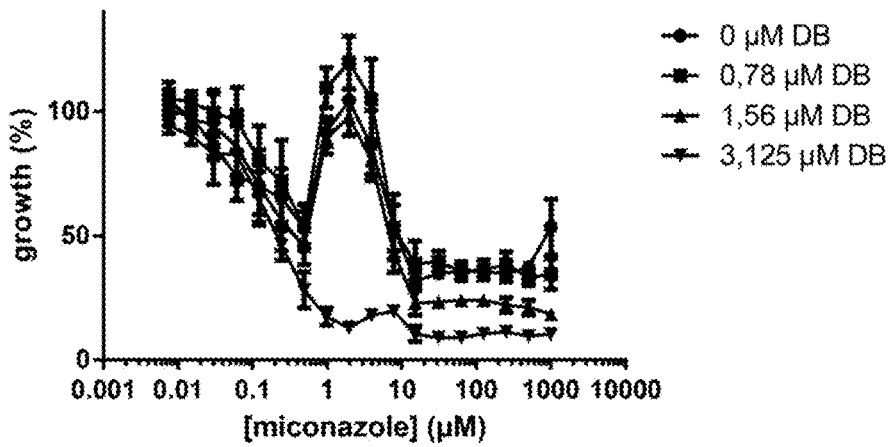
Figure 12:
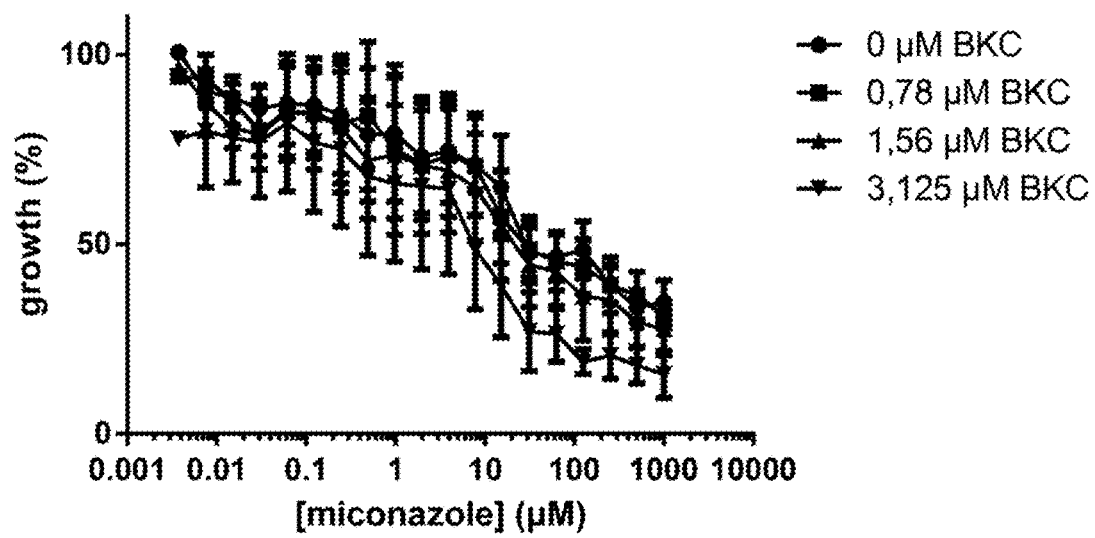

FIG. 12 shows that combined MCZ-DB treatment reduces the MIC value as compared to mono treatment of MCZ against *C. glabrata* planktonic cultures.

DEFINITIONS

About is used to described a deviation of 10% below and a above a certain value. Thus for example "about 10" means between 9 and 11, "about 50" means between 45 and 55.

Miconazole (((RS)-1-[2-(2,4-dichlorofenyl)-2-[(2,4-dichlorofenyl) methoxy] ethyl] imidazole) is an antifungal compound which interferes with the metabolism of ergosterol, a component of the yeast cell membrane. The compound is typically formulated as its nitrate.

Domiphen bromide [N,N-dimetyl-N-(2-phenoxyetyl)-, bromide] is a quaternary ammonium salt with antiseptic properties.

Viscosity in the context of the present invention refers to resistance to gradual deformation by shear stress. Viscosity can be measured by e.g. a Brookfield HA viscometer.

Fungal infection refers to a disease caused by one or more selected from the list comprising *Candida* spp., *Aspergillus* spp., *Cryptococcus* spp., *Pneumocystis* spp., *Zygomyces* spp., *Dermatophytes*, *Blastomyces* spp., *Histoplasma* spp., *Coccidoides* spp., *Sporothrix* spp., *Microsporidia* spp., *Malassezia* spp. and *Basidiomycetes*.

Typically the infection are caused by *Candida* sp. such as *Candida albicans* and *Candida glabrata*.

Biofilm refers to a mode of microbial growth comprising sessile cells, usually within a complex and highly heterogeneous matrix of extracellular polymers, and characterized by a reduced sensitivity to antifungal agents. Biofilms can contain single species (e.g. a fungi/yeast such as *C. albicans*) or multiple species microorganisms (such as *C. albicans*, *C. glabrata* and other microorganisms, preferably yeasts and/or fungi or even prokaryotes). In a preferred embodiment said biofilm is a fungal biofilm, more preferably a *Candida* species biofilm, comprising one or more of *C. albicans, C. glabrata,* and/or *C. cruse*. Biofilms may also comprise or consist of an *Aspergillus* species (e.g. *A. flavus, A. fumigatus, A. clavatus*) biofilm or a *Fusarium* species (e.g. *F. oxysporum, F. culmorum*). In the context of the present invention biofilm typically refers to a *Candida* albicans biofilm.

The compositions of the present invention generally comprise miconazole and domiphen bromide in concentrations that provide a synergistic effect. Synergy occurs when FICI values of 0,5 or less (less than 0,45, or less than 0,4) are encountered. The measurement of FICI values is explained in the examples section.

The compositions of the present invention can applied as a gels or cream.

Creams are now in the art as oil in water (o/w) or water in oil (w/o) emulsions. They typically contain an emulsifier and a thickener.

Gels are known in the art as transparent preparations containing cellulose ethers or carbomer in water or a water-alcohol mixture.

Treatment in the context of the present invention refers to a complete or partial reduction of yeast and/or a reduction in the symptoms of a fungal infection such as itching, burning with urination, and vaginal discharge.

These formulations allow at the one hand the easy removal of the composition from a tube or syringe and on the other hand ensures that the composition remains attached at the site of application.

The compositions of the present invention are in general for topical use and formulated to be compatible with the specific site of application (skin, nails, hair). For vulvovaginal applications the composition is formulated as an acidic composition at a pH between 2,75 and 3,5. The use of benzoic acid is well known in the art. Other suitable buffers which can be used in pharmaceutical compositions to obtain an acidic pH are e.g. HCl and lactic acid.

Since domiphen bromide is highly soluble in water and miconazole and its salts are insoluble in water, the compositions of the present invention are preferably a cream with an emulsifying agent, since miconazole and miconazole nitrate are insoluble in water and domiphen bromide is highly soluble in water.

Various oil/in water emulsions are known in the art. In the formulations of the present invention liquid paraffin and lauroyl macrogol-6 glycerides are typically used as oily phase.

To stabilise the emulsion emulsifiers such as for example a mixture of polyethylene glycol-6, palmitostearate, ethylene glycol stereate and PEG-32 stereate can be used.

To increase the viscosity of the emulsion, thickening agents such as cetostearyl can be used.

For optimal attachment to the site of application formulations further may comprise a mucoadhesive. Suitable mucoadhesives for vulvovaginal application includes polymers that are capable of forming hydrogels such as synthetic polycarbophil, chitosan, cellulose derivatives (hydroxyethycellulose, hydroxypropylcellulose and hydroxypropylmethylcellulose), pectin, hyaluronic acid derivatives, polyacrylates, tragacanth, carrageenan and sodium alginate, thiolated polymers.

The pharmaceutical applications can be used as a prophylactic, but are typically used upon signs of a fungal infections. Application of the pharmaceutical composition on the infected region can be performed e.g. every two days, daily or twice three times daily for a period of e.g. at least 7, 14 or 21 days, or until signs of infection have disappeared.

The compositions of the present invention are equally suitable for the treatment of recurrent vulvovaginal candidiasis (i.e. at least four specific episodes occur in one year or at least three episodes unrelated to antibiotic therapy occur within one year). The compositions of the present invention are suitable for recurrent infection with C. albicans and specifically suitable for recurrent infections with C. tropicalis or C. glabrata, which are less sensitive to miconazole monotherapies.

Pharmaceutical compositions of the present invention comprise between about 1% (w/w) to about 5% (w/w/) miconazole or a salt thereof (typically nitrate). Specific embodiments refer to about 1% (w/w/), about 1,5% (w/w), about 2% (w/w/) about 2,5% (w/w), about 3% (w/w/), about 4%, or about 5% (w/w/) miconazole nitrate.

The amount of miconazole or its salt in the pharmaceutical compositions of the present is in a molar excess of about 2, about 2,5, about 3, about 3,5 or about 4, over the amount of domiphen bromide.

Thus for example a pharmaceutical composition with a 3 fold molar excess comprising a 10 millimolar domiphen bromide contains 30 millimolar miconazole nitrate.

Any combination of the above mentioned concentrations miconazole or salt and above mentioned values of molar excess are disclosed herewith.

Specific embodiments refer to pharmaceutical compositions with about 2% (w/w) miconazole nitrate with a 3 fold molar excess over domiphen bromide.

EXAMPLES

Example 1: Materials and Methods

Strains and chemicals. C. albicans strain SC5314 was grown routinely on YPD (1% yeast extract, 2% peptone (International Medical Products, Belgium) and 2% glucose (Sigma-Aldrich, USA)) agar plates at 30° C. Stock solutions of miconazole (MCZ) (Sigma-Aldrich) were prepared in DMSO (VWR International, Belgium). RPMI 1640 medium (pH 7.0) with L-glutamine and without sodium bicarbonate was purchased from Sigma-Aldrich and buffered with MOPS (Sigma-Aldrich). Domiphen bromide was purchased from Selleck Chemicals and benzalkonium chloride, benzethonium chloride, tetraethylammonium chloride from TCI Europe (Belgium).

Antibiofilm screening assay. A C. albicans SC5314 overnight culture, grown in YPD, was diluted to an optical density of 0.1 (approximately $10^6$ cells/mL) in RPMI medium and 100 µL of this suspension was added to the wells of a round bottomed microplate (TPP Techno Plastic Products AG, Switzerland) (30, 31). After 1 h of adhesion at 37° C., the medium was aspirated and biofilms were washed with 100 µL phosphate buffered saline (PBS) to remove non-adherent cells, followed by addition of 100 µL RPMI 1640 medium. Biofilms were allowed to grow for 24 h at 37° C. Afterwards, 10 µM of Miconazole was added in combination with 25 µM of a compound from the Pharmakon 1600 library (2 mM stock solution in DMSO) in RPMI, resulting in 1.1% DMSO background. Biofilms were incubated for an additional 24 h at 37° C. Finally, biofilms were washed and quantified with Cell-Titre Blue (CTB; Promega, USA) (32) by adding 100 µL CTB diluted 1/10 in PBS to each well. After 1 h of incubation in the dark at 37° C., fluorescence was measured with a fluorescence spectrometer (Synergy Mx multi-mode microplate reader, BioTek, USA) at $\lambda_{ex}$ 535 nm and $\lambda_{em}$ 590 nm. Fluorescence values of the samples were corrected by subtracting the average fluorescence value of CTB of uninoculated wells (blank). Percentage of metabolically active biofilm cells was calculated relative to the control treatment (1.1% DMSO). Compounds were considered for retesting when their application in the presence of 10 µM Miconazole resulted in less than 60% residual metabolic activity of C. albicans biofilm cells compared to the Miconazole control. This confirmation experiment was performed twice and compound-only controls were included.

Biofilm checkerboard assay. In order to determine possible synergistic interactions between antifungal agents on one hand and identified potentiators on the other hand, a checkerboard assay was used. A combination of antifungal compound (Miconazole, fluconazole, caspofungin or amphotericin B) and potentiator, two-fold diluted across rows and columns of a microplate respectively, was added to C. albicans biofilms grown as described above (DMSO background 0.6%). After 24 h of incubation at 37° C., biofilms were quantified with the CTB method as described above. Synergism was determined by FICI (fractional inhibitory concentration index) calculations.

The FICI was calculated by the formula FICI=[C(BEC-$2_A$)/BEC-$2_A$]+[C(BEC-$2_B$)/BEC-$2_B$], in which C(BEC-$2_A$) and C(BEC-$2_B$) are the BEC-2 values of the antifungal drugs in combination, and BEC-$2_A$ and BEC-$2_B$ are the BEC-2 values of antifungal drugs A and B alone. BEC-2 stands for biofilm eradication concentration 2 which is the minimal concentration of a compound that causes a 2-fold decrease in biofilm metabolic activity.

The interaction was defined as synergistic for a value of FICI≤0.5, indifferent for 0.5<FICI<4 and antagonistic for FICI≥4.

PI assay and CFU determination. Biofilms were grown as described above and treated with selected doses of Miconazole and either domiphen bromide, benzalkonium chloride, bezethonium chloride, dequalinium chloride or tetraethylammonium bromide. To obtain a kinetic PI read out, biofilms were incubated, in the presence of 3% PI, in a multimode reader (Syngergy MX, Biotek) which measures fluorescence each 15 min during 17 h (emission wavelength: 535 nm and excitation wavelength: 617 nm). CFU determination was performed on biofilms 24 h after treatment. To this end, biofilms were washed with PBS and thoroughly scraped off the bottom of the plate. Serial dilutions were plated on YPD agar plates and incubated for 48 h at 30° C. before colony counting.

Example 2: Screening for Potentiators of Miconazole Against *C. albicans* Biofilms Domiphen bromide (DB), was tested for its capacity to reduce *C. albicans* biofilm metabolic activity with more than 50% in combination with a subinhibitory Miconazole dose and its toxicity profile on human cells.

Figure 1:
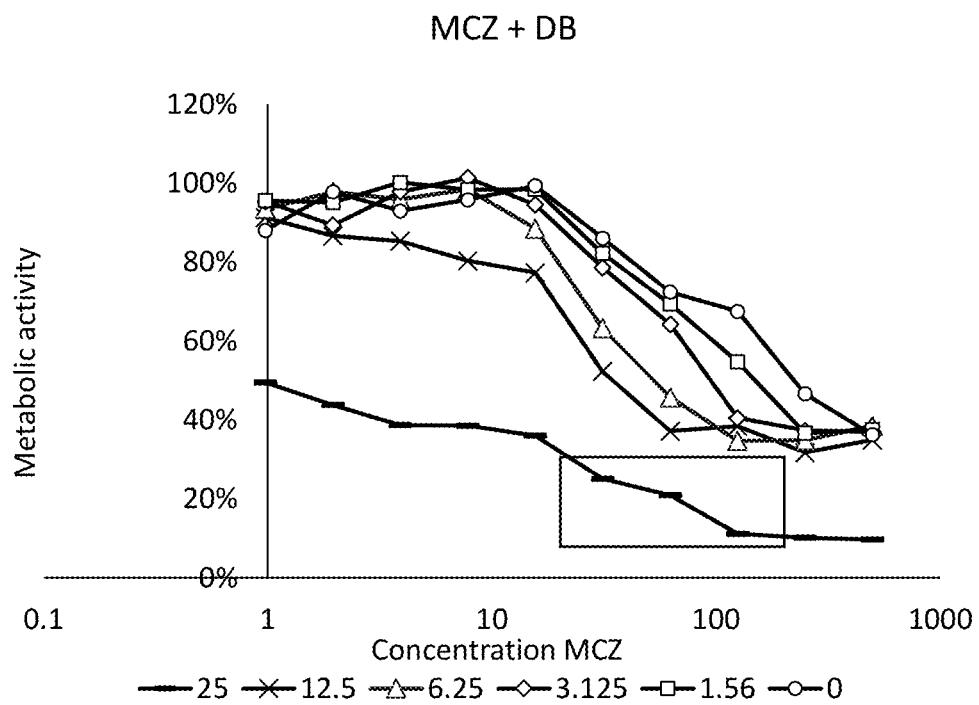

Example 3: Quaternary Ammonium Compounds Act Synergistically with Miconazole Against *C. albicans* Biofilms To determine whether domiphen bromide acts synergistically with Miconazole against *C. albicans* biofilms, checkerboard experiments (FIG. 1) and FICI calculations were performed (Table 1). The checkerboard data show that, in the presence of domiphen bromide, lower concentrations of Miconazole can be used to reduce the metabolic activity of *C. albicans* biofilms, indicative for decreased survival of the biofilm cells (FIG. 1). Next, we derived the concentration of both Miconazole and domiphen bromide necessary to eradicate the *C. albicans* biofilm with 50% or 2-fold (Biofilm-Eradication-Concentration-2, BEC-2), to enable FICI calculations (Table 1).

TABLE 1

Synergistic Miconazole-domiphen bromide combinations against *C. albicans* biofilms

| Concentration DB (μM) | BEC-2 MCZ (μM) | FICI* |
|---|---|---|
| 25 | 1 | 0.740 |
| 12.5 | 30 | 0.498 ## |
| 6.25 | 55 | 0.423 ## |
| 3.125 | 100 | 0.527 |
| 1.56 | 150 | 0.698 |
| 0 | 230 | Not applicable |

*FICI calculations are based on the formula FICI = [C(BEC-2A)/BEC-2A] + [C(BEC-2B)/BEC-2B], in which C(BEC-2A) and C(BEC-2B) are the BEC-2 values of Miconazole in combination and BEC-2A and BEC-2B are the BEC-2 values of Miconazole (230 μM) and domiphen bromide (33 μM) alone.
synergistic values For concentrations of 12.5 μM and 6.25 μM domiphen bromide, synergy was observed (FICI<0.5) in combination with Miconazole against *C. albicans* biofilms (Table 1). Synergistic combinations were found for combinations of domiphen bromide and Miconazole in a ratio of 1/9 to 1/2.3.

Figure 2:
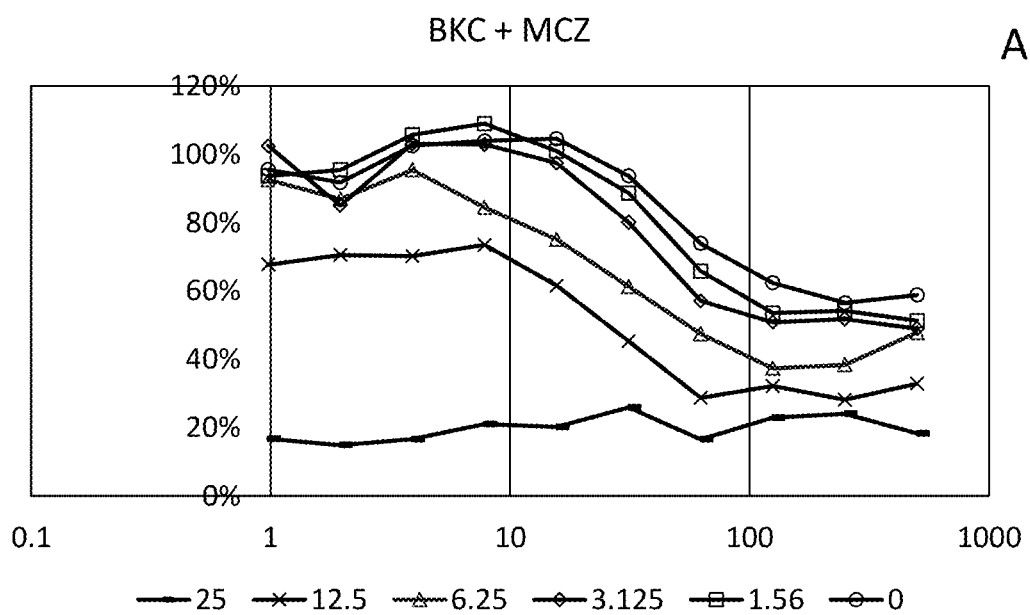
Figure 2:
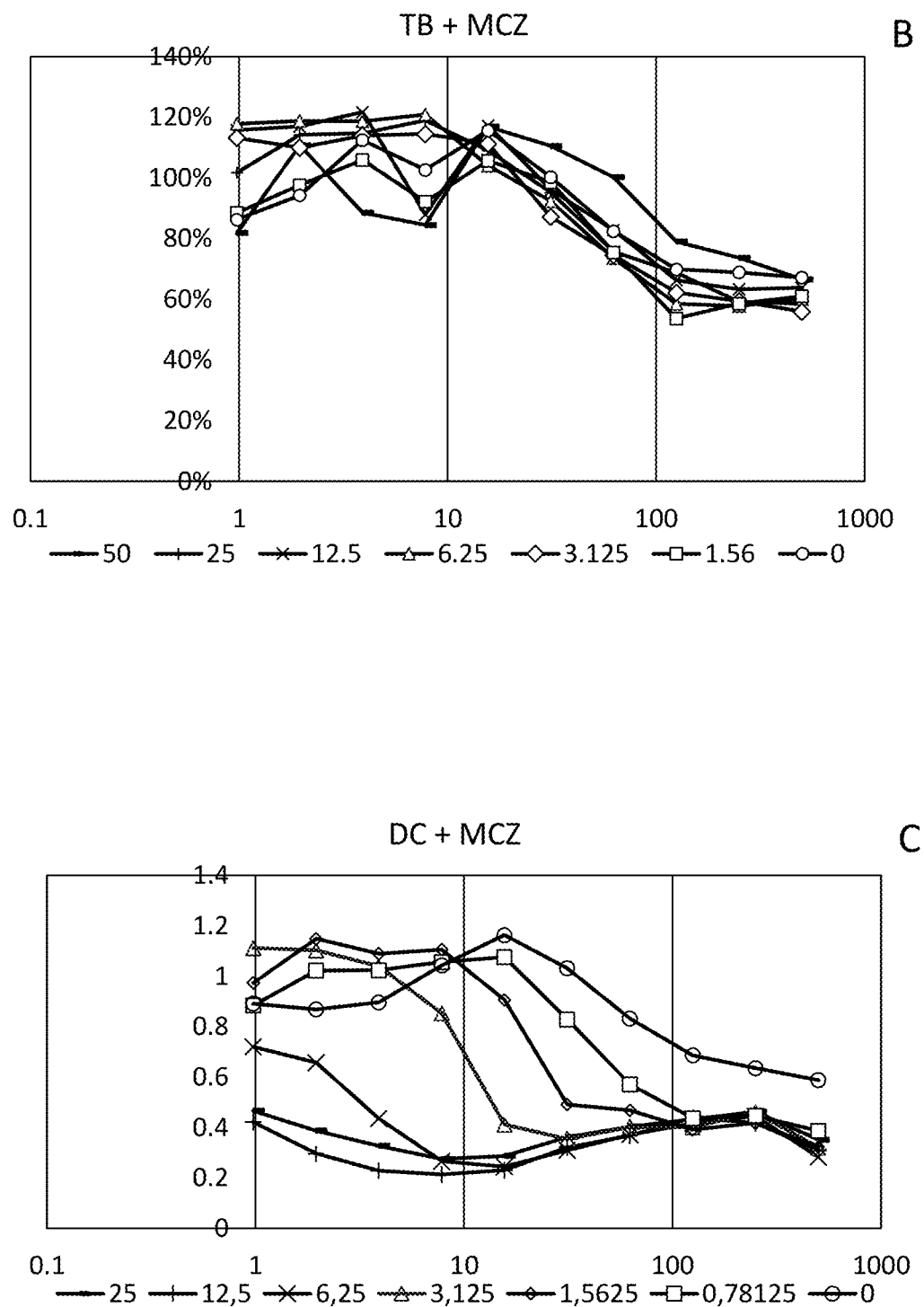

To our interest, we previously detected other quaternary ammonium compounds as potential Miconazole potentiators, namely benzalkonium chloride (BKC) and bezethonium chloride (BTC) (unpublished data). However, their activity in combination with Miconazole was never assessed in checkerboard analyses. Therefore, in this study, we assessed potential synergistic interactions between Miconazole and various quaternary ammonium compounds, including benzalkonium chloride, bezethonium chloride, dequalinium chloride (DC) and tetraethylammonium bromide (TB) (FIG. 2).

We found that benzalkonium chloride, bezethonium chloride and dequalinium chloride act synergistically with Miconazole (FICI<0.5), while this is not the case for tetraethylammonium bromide (FICI>0.5). These data suggest that the synergistic action with Miconazole is a characteristic of various quaternary ammonium compounds, implying that the activity is probably attributed to the core chemical structure of this family.

Figure 3:
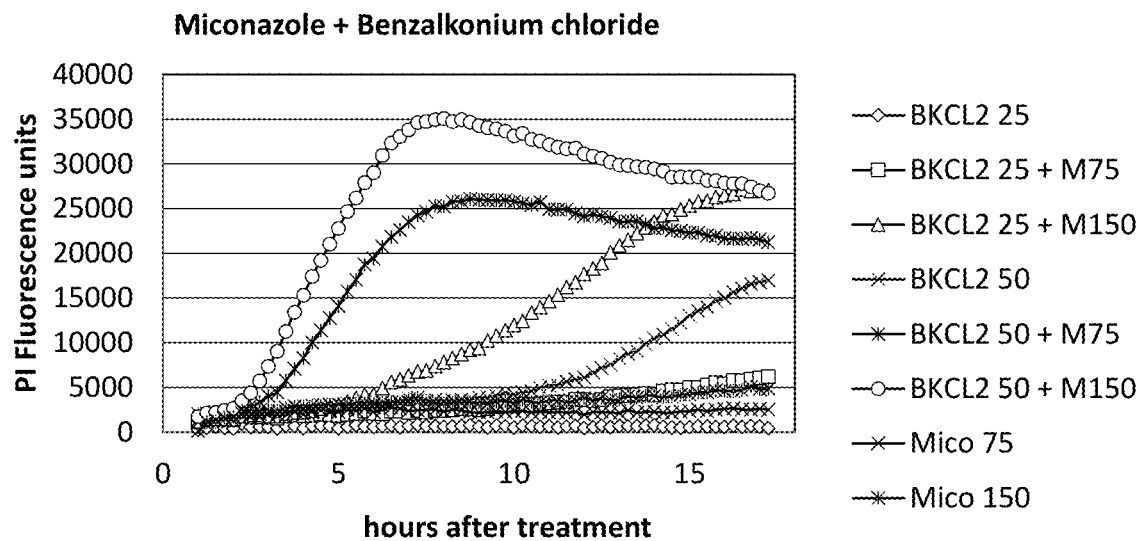
Figure 3:
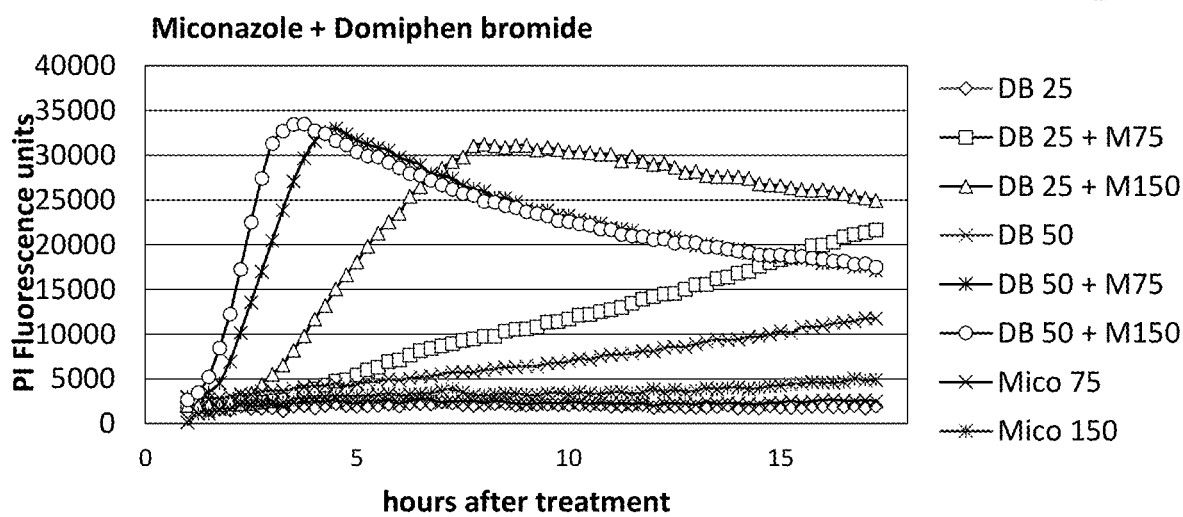
Figure 3:
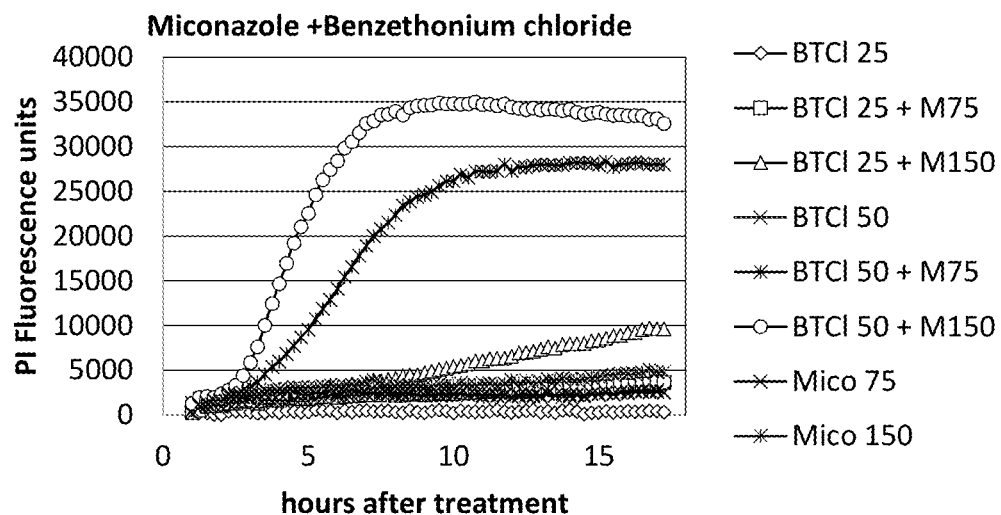
Figure 3:
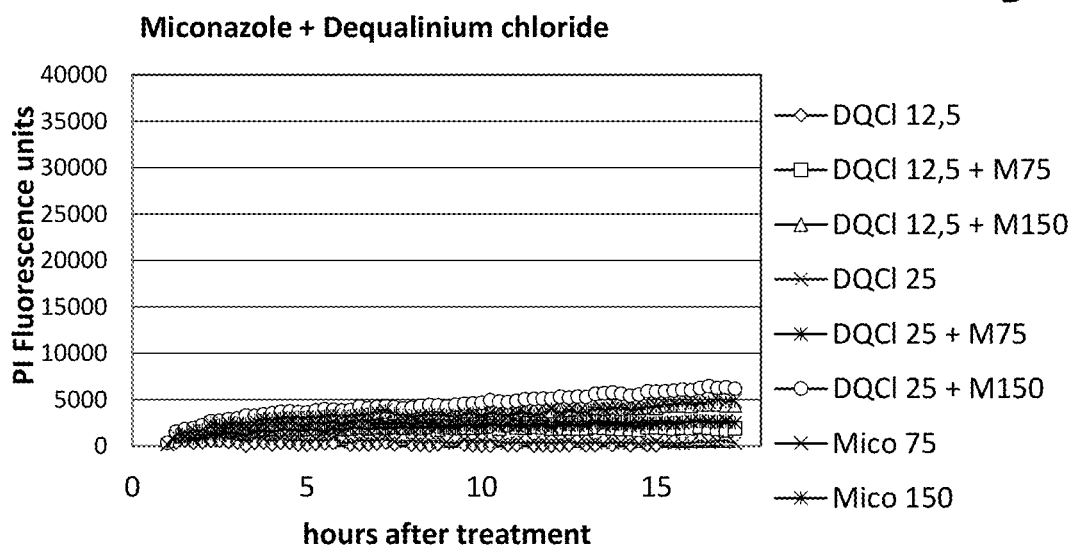

Example 4: The Domiphen Bromide—Miconazole and Benzalkonium Chloride—Miconazole Combinations Show Prominent Fungicidal Activity Against *C. albicans* Biofilms A reduction in metabolic activity, as observed in the previous experiments, does not necessarily mean that the biofilm cells under investigation are dead. It could very well be that their cellular metabolism is attenuated in the presence of the compounds, but that they revive when the stress is removed. To assess how much damage is actually caused to the cells and in what time frame, we performed a time-course experiment on *C. albicans* biofilms treated with a combination of domiphen bromide, benzalkonium chloride, bezethonium chloride or dequalinium chloride (25 μM or 50 μM) and Miconazole (75 μM or 150 μM) (resulting in a 1/3 ratio) or single compounds, in the presence of propidium iodide (PI) (FIG. 3). The concentrations of the compounds were chosen based on the observation in FIG. 1 that 25 μM domiphen bromide in combination with 500, 250, 125 or 62.5 μM Miconazole resulted in a reduction of *C. albicans* biofilm metabolic activity below 25% (box in FIG. 1).

PI is known to permeate through the membrane of damaged cells and its uptake is an indication of cell death. We observed only a slight increase in PI fluorescence when cells were treated with 150 μM Miconazole after 16 h of treatment. Among the single treatments with the quaternary ammonium compounds, only domiphen bromide and benzalkonium chloride showed a slight increase in PI fluorescence 5-10 h after treatment at 50 μM. However, the fastest effect is observed for combinations of Miconazole with either 50 μM domiphen bromide, benzalkonium chloride or bezethonium chloride, with PI values starting to increase already 2-3 h after treatment. Remarkably, no additional increase in PI fluorescence could be observed for combinations of Miconazole and dequalinium chloride (FIG. 3). Remarkably, no increase was observed for dequalinium chloride, but combinations with 50 μM are lacking.

Figure 4:
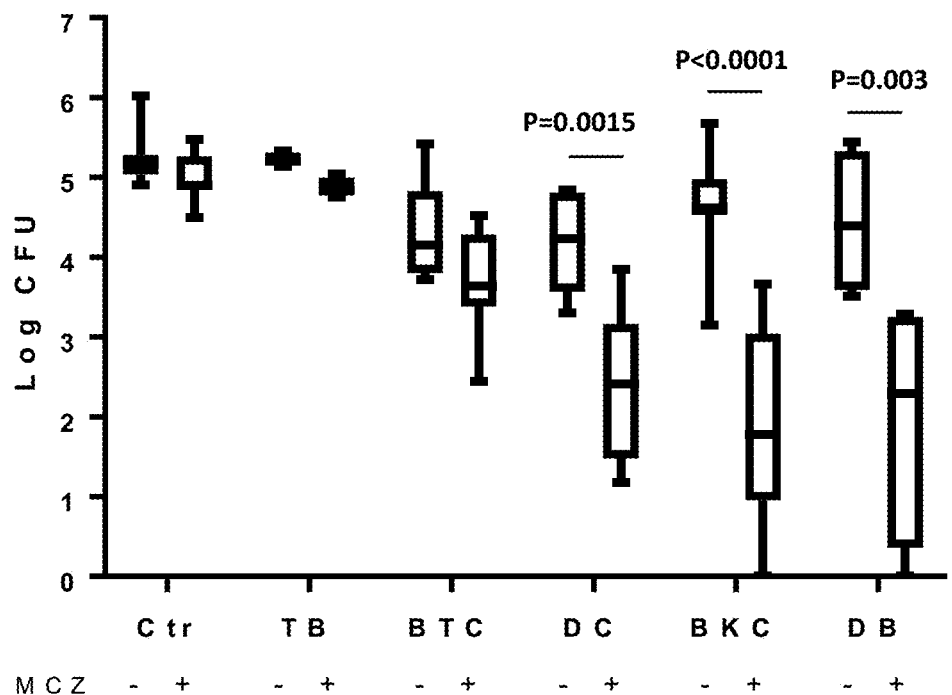

The killing capacity of the quaternary ammonium compounds in the presence or absence of Miconazole was further confirmed by CFU counting for selected doses of the compounds (FIG. 4).

Therapeutically interesting reductions in CFUs (>3 Log units) were only observed for combinations of 150 μM Miconazole with 50 μM benzalkonium chloride and 50 μM domiphen bromide (FIG. 4). Interestingly, in a few cases, complete sterility of the surface was observed after treatment with these combinations.

Example 5: The Observed Synergy Between Quaternary Ammonium Compounds and Miconazole is Miconazole-specific We assessed whether the quaternary ammonium compound could also increase the activity of fluconazole against *C. albicans* biofilms. Fluconazole showed no significant antibiofilm activity on its own nor in combination with 25 µM domiphen bromide, benzalkonium chloride, bezethonium chloride or dequalinium chloride (BEC-2>500 µM) (data not shown).

Example 6: Formulations for Vulvovaginal Application

The example illustrates the preparation of different pharmaceutical compositions comprising domiphen bromide and/or miconazole.

TABLE 2 formulation of domiphen bromide and/or miconazole compositions.

| Excipiënt (property) | F1 Placebo (w/w %) | F2 2% MCZ nitrate (w/w %) | F3 4% MCZ nitrate (w/w %) | F4 domiphen bromide (w/w %) | F5 2% MCZ nitrate + 3/1 domiphen bromide (w/w %) |
|---|---|---|---|---|---|
| Mixture of PEG-6 palmitostearate, ethylene glycol stearate and PEG-32 stearate (O/W emulsifier) | 12.00 | 11.76 | 11.52 | 11.93 | 11.69 |
| Lauroyl macrogol-6 glycerides (Oily phase) | 3.00 | 2.94 | 2.88 | 2.98 | 2.92 |
| Cetostearyl alcohol (thickener) | 2.00 | 1.96 | 1.92 | 3.98 | 3.90 |
| liquid paraffine (Oily phase) | 8.00 | 7.84 | 7.68 | 7.95 | 7.79 |
| Water (Aqueous phase) | 75.00 | 73.50 | 72.00 | 72.58 | 71.12 |
| Miconazole nitrate | 0.00 | 2.00 | 4.00 | 0.00 | 2.00 |
| Domiphen bromide | 0.00 | 0.00 | 0.00 | 0.58 | 0.58 |

In F5 miconazole nitrate is in a 3 fold molar excess over domiphen bromide

Example 7: Animal Model for Vaginal *Candida* Infection

The above F5 formulation is a miconazole nitrate-domiphen bromide preparation with in vitro synergistic effect (3 fold molar excess of domiphen bromide over miconazole nitrate) is tested is a rat model.

F1 to F4 are controls with no active ingredient (F1) miconazole nitrate (F2 and F3) and domiphen bromide (F4)

Female Wistar rats (180-200 g) are kept in groups of 4 animals. Food and water is available ad libitum. Husbandry conditions are: room temperature 22° C., humidity 60% and a day-night cycle of 12 h light/12 h dark.

Preconditioning

The rats are ovariectomized 2 to 3 weeks before infection under inhalation—anesthesia with isoflurane. During recovery, the rats are put under an IR-lamp for about 30 minutes. Three days before infection, the animals receive 1 mg oestradiolbenzoate in 0.1 ml PEG400 SC and 200 µg progesteron in 0.1 ml PBS SC to induce artificial estrus (given as 1 injection). This injection is repeated twice during the experiment.

Preparation of Inoculum and Infection Procedure

*Candida albicans* B2630-cryostock is used for the infection. Each vial contains 1 ml RPMI with 10% glycerol with an inoculum size of 5.108 cfu/ml. A dilution of 1/5 in sterile water is made prior to infection. The animals are infected with 1.107 cfu in 100 µl using a micropipette with disposable tips. The end of the tip is inserted into the vagina and the rat is held slightly up by the tail for about one minute after instillation.

Treatment Groups

Topical b.i.d. treatment is started on the morning after the infection (D1) for 4 days (200 µl/animal, applied by inserting the tip of a 1 ml syringe into the vagina).

The following formulations have been used. (details of these formulations are shown above in table 2).

G1a: Formulation 1a or Vehicle-treated infected control (VICa): b.i.d. (200 µL) (#2)

G1b: Formulation 1b or Vehicle-treated infected control (VICb): b.i.d. (200 µL) (#2)

G2: Formulation 2 (Miconazole nitrate): b.i.d. Top 2% for 4 days (200 µL) (#4)

G3: Formulation 3 (Miconazole nitrate): b.i.d. Top 4% for 4 days (200 µL) (#4)

G4: Formulation 4 (Domiphen bromide): b.i.d. Top for 4 days (200 µL) (#4)

G5: Formulation 5 (Miconazole nitrate/Domiphen bromide): b.i.d. 4 days (200 µL) (#4)

Evaluation Parameters

Estrus control: on days 4, 9 and 14, vaginal smears are taken with a moist swab and stained with Giemsa to check the artificial estrus (microscopic count of cornified epithelial cells). On days 2 and 7, the hormone injections are repeated in order to maintain a continuous estrus.

Body weight: follow up of body weight (BW) and calculation of percentage gain or loss in comparison to BW before infection (day 0).

Vaginal yeast burdens: vaginal samples are collected on days 4, 9 and 14. A sterile swab is moistened in sterile water, inserted into the vagina and rotated twice. The swab is then brought into a tube with 1 ml sterile water and put on the vortex stirrer for 40 seconds. Ten-fold dilutions of this solution are prepared and plated on a Sabouraud agar. After 24-48 h incubation at 37° C., the colonies are counted and the number of cfu's/ml is calculated as a measure for the total intravaginal burden. The results are expressed as a LOG function of the number of cfu's that was found on the swab (except when no colonies, where the result=0).

Results

As there was no differences between both vehicle control groups 1a and 1b, both groups were combined and shown as Group 1.

Estrus Control

High levels of cornified epithelial cells were observed throughout the experiment (Table 3), confirming permanent estrus.

TABLE 3

Percentages of cornified epithelial cells observed throughout the experiment on several days p.i.

|  | R1 | R2 | R3 | R4 | Average |
|---|---|---|---|---|---|
| G1 | | | | | |
| Day 0 | 99% | 95% | 99% | 95% | 97% |
| Day 4 | 90% | 90% | 95% | 95% | 93% |
| Day 9 | 90% | 80% | 95% | 90% | 89% |
| G2 | | | | | |
| Day 0 | 99% | 95% | 95% | 99% | 97% |
| Day 4 | 90% | 99% | 95% | 99% | 96% |
| Day 9 | 90% | 90% | 80% | 40% | 75% |
| G3 | | | | | |
| Day 0 | 95% | 99% | 95% | 90% | 95% |
| Day 4 | 99% | 99% | 90% | 95% | 96% |
| Day 9 | 50% | 90% | 95% | 20% | 64% |
| G4 | | | | | |
| Day 0 | 100% | 99% | 99% | 95% | 98% |
| Day 4 | 90% | 90% | 95% | 50% | 81% |
| Day 9 | 50% | 95% | 85% | 95% | 81% |
| G5 | | | | | |
| Day 0 | 99% | 99% | 99% | 95% | 98% |
| Day 4 | 90% | 80% | 50% | 90% | 78% |
| Day 9 | 90% | 90% | 60% | 95% | 84% |

G: treatment group,
R: animal number.

Body Weight

The standard deviation of the average body weight per animal remained constant during the course of infection (Table 4), indicating that no severe weight loss occurred.

TABLE 4

Evolution of live body weight (g) of rats upon vaginal infection with *Candida albicans*

|  | day 1 (g) | day 2 (g) | day 3 (g) | day 4 (g) | day 15(g) | Average (g) | SD (g) |
|---|---|---|---|---|---|---|---|
| G1 R1 | 258 | 251 | 254 | 245 | 255 | 253 | 5 |
| R2 | 253 | 247 | 253 | 244 | 248 | 249 | 4 |
| R3 | 261 | 254 | 253 | 245 | 242 | 251 | 8 |
| R4 | 282 | 275 | 280 | 271 | 276 | 277 | 4 |
| G2 R1 | 266 | 258 | 256 | 250 | 252 | 256 | 6 |
| R2 | 275 | 272 | 270 | 264 | 264 | 269 | 5 |
| R3 | 264 | 257 | 260 | 252 | 253 | 257 | 5 |
| R4 | 248 | 243 | 246 | 241 | 239 | 243 | 4 |
| G3 R1 | 276 | 271 | 270 | 265 | 264 | 269 | 5 |
| R2 | 262 | 254 | 256 | 246 | 254 | 254 | 6 |
| R3 | 264 | 260 | 266 | 256 | 255 | 260 | 5 |
| R4 | 244 | 238 | 241 | 232 | 235 | 238 | 5 |
| G4 R1 | 252 | 244 | 247 | 238 | 244 | 245 | 5 |
| R2 | 273 | 268 | 272 | 252 | 264 | 266 | 8 |
| R3 | 261 | 254 | 258 | 251 | 263 | 257 | 5 |
| R4 | 261 | 252 | 256 | 245 | 244 | 252 | 7 |
| G5 R1 | 240 | 241 | 244 | 235 | 232 | 238 | 5 |
| R2 | 245 | 237 | 243 | 231 | 233 | 238 | 6 |
| R3 | 265 | 255 | 258 | 251 | 249 | 256 | 6 |
| R4 | 236 | 235 | 237 | 230 | 232 | 234 | 3 |

G: treatment group,
R: animal number,
SD: standard deviation.

Vaginal Yeast Burden

Figure 5:
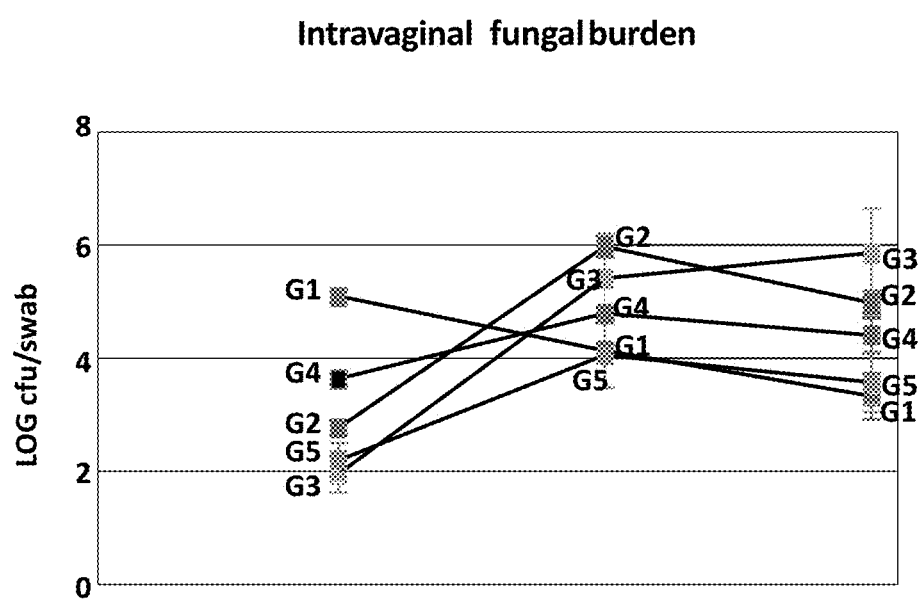
Figure 6:
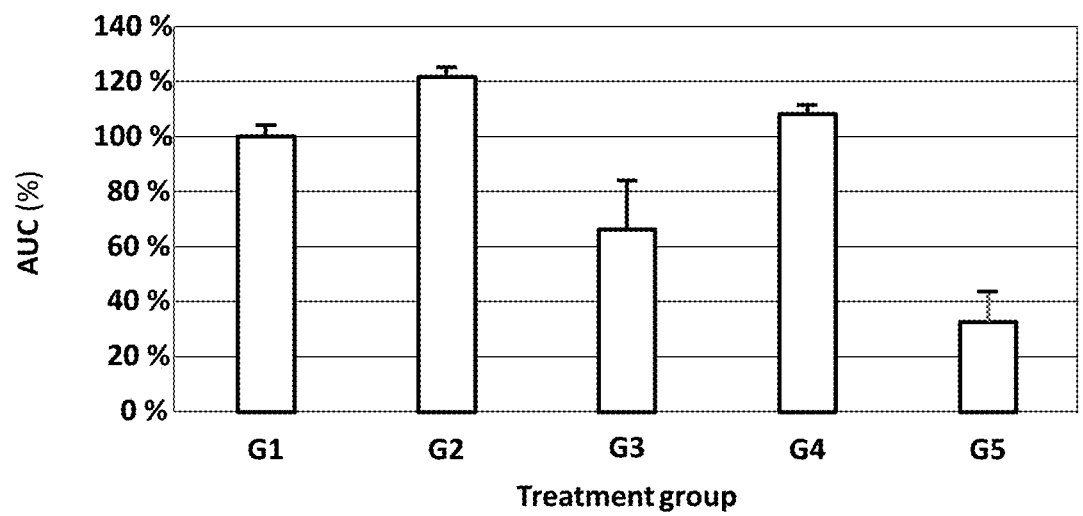

The infection is measured by counting the intravaginal fungal burden of each swab (FIG. 5) and calculating the area under the curve (AUC) (FIG. 6). This method allows comparison of the total infection of several treatment groups to the control group, while cfu counts allow for a comparison at several time points p.i. The AUC clearly shows that 2% miconazole doesn't affect the outcome of the infection, while 4% miconazole has a positive effect (33% reduction in AUC). The potentiator DOM by itself doesn't influence the outcome of the infection, while the combination of 2% MIC+DOM reduces AUC of the infection by 66%.

Under the stated experimental conditions, an antifungal effect of miconazole when used at 4% could be demonstrated. No antifungal effect was observed for miconazole at 2%, but a significant effect was seen when the potentiator domiphen bromide was added, although domiphen bromide itself does not influence the outcome of the infection.

Example 8: Vaginal *Candida* Infection (II)

Animals, preconditioning, preparation of inoculum and infection procedure is as described in example 7.

Treatment Groups

Topical b.i.d. treatment is started on thee morning after the infection (D1) for 4 days (200 μl/animal, applied by inserting the tip of a 1 ml syringe into the vagina)

G1: Formulation 1 or Vehicle-treated infected control (VIC): b.i.d. (200 μL) (#4)

G2: Formulation 2 (Miconazole nitrate): b.i.d. Top 2% for 4 days (200 μL) (#9)

G3: Formulation 5 (Miconazole nitrate/⅓ mmol Domiphen bromide): b.i.d. 4 days (200 μL) (#10)

G4: Formulation 4 (⅓ mmol Domiphen bromide): b.i.d. 4 days (200 μL) (#4)

Evaluation Parameters

Estrus control, Body weight and Vaginal yeast burdens were determined as described above.

Estrus Control

High levels of cornified epithelial cells were observed throughout the experiment (Table 5, which relates to estrus. It should be noted that, for some animals in group 3, cornification seemed to lower around day 4. This is probably due to the way of sampling, which has been modified for day 9, demonstrating cornification is still in place.

TABLE 5

Percentages of cornified epithelial cells observed throughout the experiment on several days p.i.

| G1 | R1 | R2 | R3 | R4 | | | | | | Average |
|---|---|---|---|---|---|---|---|---|---|---|
| Day 0 | 99 | 100 | 100 | 100 | | | | | | 100 |
| Day 4 | 99 | 90 | 90 | 90 | | | | | | 92 |
| Day 9 | 80 | 90 | 80 | 99 | | | | | | 87 |

| G2 | R1 | R2 | R3 | R4 | R5 | R6 | R7 | R8 | R9 | Average |
|---|---|---|---|---|---|---|---|---|---|---|
| Day 0 | 99 | 100 | 90 | 100 | 100 | 99 | 99 | 100 | 100 | 99 |
| Day 4 | 80 | 90 | 90 | 99 | 90 | 60 | 80 | 99 | 99 | 87 |
| Day 9 | 20 | 99 | 95 | 90 | 99 | 0 | 95 | 0 | 99 | 66 |

| G3 | R1 | R2 | R3 | R4 | R5 | R6 | R7 | R8 | R9 | R10 | Average |
|---|---|---|---|---|---|---|---|---|---|---|---|
| Day 0 | 99 | 100 | 100 | 100 | 100 | 100 | 99 | 95 | 95 | 95 | 98 |
| Day 4 | 80 | 90 | 40 | 50 | 90 | 80 | 60 | 20 | 30 | 50 | 59 |
| Day 9 | 100 | 100 | 90 | 90 | 99 | 99 | 100 | 90 | 99 | 90 | 96 |

| G4 | R1 | R2 | R3 | R4 | | | | | | Average |
|---|---|---|---|---|---|---|---|---|---|---|
| Day 0 | 99 | 99 | 100 | 100 | 100 | | | | | |
| Day 4 | 80 | 90 | 90 | 60 | 80 | | | | | |
| Day 9 | 90 | 99 | 90 | 90 | 92 | | | | | |

G: treatment group,
R: animal number. (all values in percentages)

Body Weight

The standard deviation of the average body weight per animal remained constant during the course of infection (Table 6), indicating no severe weight loss occurred.

TABLE 6

Body weight (in g) of rats in several days p.i.

| | day 0 (g) | Day 1 (g) | Day 2 (g) | Day 3 (g) | Day 4 (g) | Day 7 (g) | Day 9 (g) | Day 14 (g) | Avg. (g) | SD (g) |
|---|---|---|---|---|---|---|---|---|---|---|
| G1 R1 | 238 | 241 | 238 | 232 | 220 | 228 | 232 | 222 | 231 | 8 |
| R2 | 246 | 243 | 243 | 239 | 229 | 226 | 230 | 228 | 236 | 8 |
| R3 | 259 | 256 | 256 | 247 | 242 | 249 | 252 | 254 | 252 | 6 |
| R4 | 254 | 255 | 251 | 250 | 240 | 242 | 253 | 245 | 249 | 6 |
| G2 R1 | 257 | 259 | 255 | 254 | 246 | 249 | 254 | 248 | 253 | 5 |
| R2 | 242 | 246 | 236 | 235 | 226 | 231 | 234 | 232 | 235 | 6 |
| R3 | 245 | 244 | 238 | 237 | 229 | 229 | 227 | 243 | 237 | 7 |
| R4 | 224 | 224 | 222 | 219 | 213 | 217 | 219 | 216 | 219 | 4 |
| R5 | 259 | 257 | 253 | 247 | 241 | 260 | 259 | 259 | 254 | 7 |
| R6 | 222 | 222 | 219 | 220 | 212 | 229 | 235 | 238 | 225 | 9 |
| R7 | 246 | 248 | 241 | 240 | 238 | 238 | 232 | 238 | 240 | 5 |
| R8 | 245 | 244 | 241 | 240 | 230 | 229 | 235 | 229 | 237 | 7 |
| R9 | 224 | 226 | 223 | 223 | 213 | 215 | 216 | 211 | 219 | 6 |
| G3 R1 | 243 | 235 | 235 | 232 | 224 | 231 | 239 | 237 | 235 | 6 |
| R2 | 250 | 257 | 253 | 244 | 235 | 239 | 246 | 243 | 246 | 7 |
| R3 | 254 | 254 | 255 | 246 | 237 | 239 | 246 | 226 | 245 | 10 |
| R4 | 253 | 253 | 250 | 244 | 237 | 237 | 243 | 246 | 245 | 6 |
| R5 | 266 | 265 | 256 | 255 | 251 | 255 | 262 | 262 | 259 | 5 |
| R6 | 242 | 244 | 239 | 236 | 223 | 218 | 230 | 226 | 232 | 9 |
| R7 | 263 | 265 | 256 | 256 | 244 | 250 | 258 | 257 | 256 | 7 |
| R8 | 252 | 251 | 246 | 246 | 238 | 246 | 242 | 253 | 247 | 5 |
| R9 | 212 | 230 | 228 | 227 | 218 | 229 | 235 | 238 | 227 | 8 |
| R10 | 262 | 260 | 257 | 257 | 246 | 251 | 254 | 250 | 255 | 5 |
| G4 R1 | 246 | 258 | 252 | 250 | 241 | 242 | 246 | 250 | 248 | 6 |
| R2 | 243 | 249 | 242 | 240 | 232 | 235 | 232 | 236 | 239 | 6 |
| R3 | 233 | 221 | 234 | 229 | 222 | 228 | 232 | 228 | 228 | 5 |
| R4 | 268 | 268 | 266 | 261 | 256 | 257 | 260 | 268 | 263 | 5 |

G: treatment group,
R: animal number,
SD: standard deviation.

Vaginal Yeast Burdens

Figure 8:
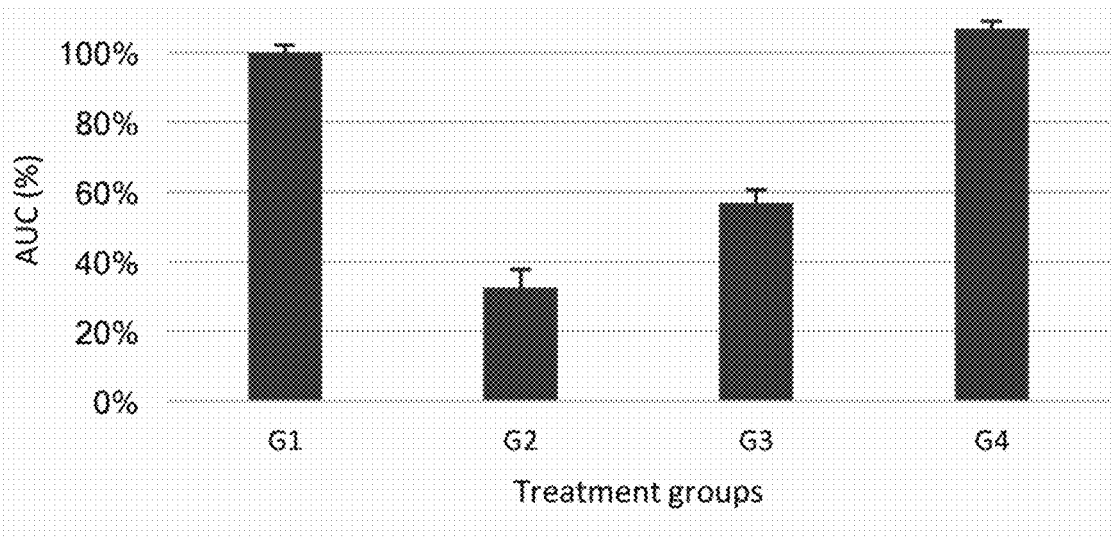
FIG. 8 shows intravaginal fungal burden of all groups. The burden is shown as the area under the curve (AUC).

The infection is measured by counting the intravaginal fungal burden of each swab (Table 7) and calculating the area under the curve (AUC) (FIG. 8). This method allows comparison of the total infection of several treatment groups to the control group, while cfu counts allow for a comparison at several time points p.i.

The AUC shows a clear effect of miconazole 2%, concurring with previous results, reducing the infection by 65%. Also concurring with previous results, the combination of 2% miconazole+potentiator reduces the AUC, but there is only a clear benefit at day 4 when compared to 2% miconazole. Concurring with the first experiment (exp. 2017-1146), domiphen by itself doesn't reduce the infection. For this experiment, no extra agitation of certain groups has been noted, as opposed to previous results.

TABLE 7

Intravaginal infection burden.

| | G1 | | | | |
|---|---|---|---|---|---|
| | 1 | 2 | 3 | 4 | avg |
| Cfu/ml (D4) | 1.02 E+04 | 4.4 E+04 | 6.00 E+05 | 3.00 E+05 | 2.39 E+05 |

TABLE 7-continued

Intravaginal infection burden.

| | | | | | | | | | | |
|---|---|---|---|---|---|---|---|---|---|---|
| Log (D4) | 4.01 | 4.64 | 5.78 | 5.48 | | | | | | 5.38 |
| Cfu/ml (D9) | 2.56 E+3 | 1.98 E+5 | 1.56 E+3 | 8.6 E+3 | | | | | | 5.27 E+4 |
| Log (D9) | 3.41 | 5.3 | 3.19 | 3.93 | | | | | | 4.75 |
| Cfu/ml (D14) | 2.04 E+5 | 8.2 E+2 | 4.00 E+1 | 3.8 E+3 | | | | | | 3.80 E+4 |
| Log (D14) | 5.31 | 0 | 1.6 | 3.58 | | | | | | 4.72 |

| G2 | | | | | | | | | | |
|---|---|---|---|---|---|---|---|---|---|---|
| | 1 | 2 | 3 | 4 | 5 | 6 | 7 | 8 | 9 | avg |
| Cfu/ml (D4) | 6.00 E+2 | 0.00 | 0.00 | 0.00 | 6.00 E+2 | 1.00 E+3 | 0.00 | 4.00 E+2 | 0.00 | 2.89 E+2 |
| Log (D4) | 2.78 | 0.00 | 0.00 | 0.00 | 2.78 | 3.00 | 0.00 | 2.60 | 0.00 | 2.46 |
| Cfu/ml (D9) | 0.00 | 7.40 E+4 | 0.00 | 0.00 | 9.2 E+5 | 0.00 | 0.00 | 0.00 | 0.00 | 1.10 E+5 |
| Log (D9) | 0.00 | 4.78 | 0.00 | 0.00 | 5.96 | 0.00 | 0.00 | 0.00 | 0.00 | 5.04 |
| Cfu/ml (D14) | 0.00 | 1.18 E+3 | 0.00 | 0.00 | 7.4 E+5 | 0.00 | 0.00 | 6.60 E+3 | 0.00 | 8.31 E+4 |
| Log (D14) | 0.00 | 3.07 | 0.00 | 0.00 | 5.87 | 0.00 | 0.00 | 3.82 | 0.00 | 4.92 |

| G3 | | | | | | | | | | | |
|---|---|---|---|---|---|---|---|---|---|---|---|
| | 1 | 2 | 3 | 4 | 5 | 6 | 7 | 8 | 9 | 10 | avg |
| Cfu/ml (D4) | 0.00 | 0.00 | 0.00 | 0.00 | 0.00 | 0.00 | 0.00 | 0.00 | 0.00 | 0.00 | 0.00 |
| Log (D4) | 0.00 | 0.00 | 0.00 | 0.00 | 0.00 | 0.00 | 0.00 | 0.00 | 0.00 | 0.00 | 0.00 |
| Cfu/ml (D9) | 4.4 E+03 | 0.00 | 7.20 E+04 | 1.48 E+05 | 8.6 E+04 | 4.80 E+02 | 1.72 E+04 | 0.00 | 0.00 | 1.00 E+02 | 3.82 E+04 |
| Log (D9) | 3.64 | 0.00 | 4.86 | 5.17 | 4.93 | 2.68 | 4.24 | 0.00 | 0.00 | 2.00 | 4.52 |
| Cfu/ml (D14) | 3.60 E+03 | 0.00 | 1.66 E+05 | 1.64 E+05 | 1.98 E+05 | 0.00 | 2.12 E+04 | 1.30 E+05 | 0.00 | 1.86 E+04 | 7.01 E+04 |
| Log (D14) | 3.56 | 0.00 | 5.22 | 5.21 | 5.30 | 0.00 | 4.33 | 5.11 | 0.00 | 4.27 | 43.85 |

| G4 | | | | | |
|---|---|---|---|---|---|
| | 1 | 2 | 3 | 4 | avg |
| Cfu/ml (D4) | 1.22 E+03 | 1.6 E+02 | 7.60 E+03 | 5.00 E+03 | 3.5 E+03 |
| Log (D4) | 3.09 | 2.20 | 3.88 | 3.70 | 3.54 |
| Cfu/ml (D9) | 4.80 E+04 | 4.00 E+05 | 1.42 E+05 | 3.20 E+04 | 1.56 E+05 |
| Log (D9) | 4.68 | 5.60 | 5.15 | 4.51 | 5.19 |
| Cfu/ml (D14) | 1.56 E+3 | 5.40 E+4 | 1.18 E+3 | 3.20 E+2 | 1.43 E+4 |
| Log (D14) | 3.19 | 4.73 | 3.07 | 2.51 | 4.15 |

Figure 7:
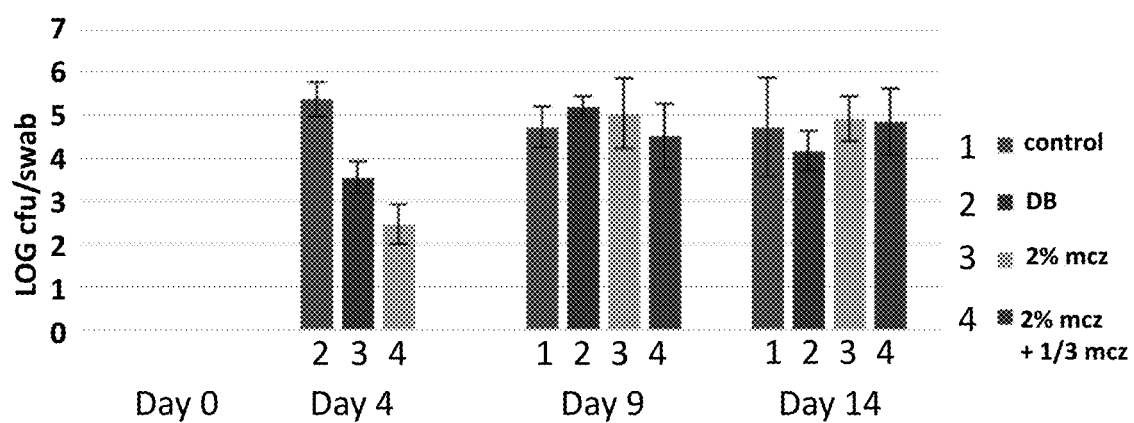
FIG. 7 shows intravaginal fungal burden of all groups at different days p.i.

FIG. 7 shows the intravaginal fungal burden of all groups at different days p.i. The burden is shown as the log of the colony forming units (cfu) present on the vaginal swab. Errors bars represent SEM. FIG. 8 shows Intravaginal fungal burden of all groups. The burden is shown as the area under the curve (AUC) compared to the control group (G1) (=100%) is shown as the log of the colony forming units (cfu) present on the vaginal swab. Errors bars represent SEM. G: treatment group.

Both miconazole 2% and miconazole 2% combined with domiphen reduce the infection. At day 4, there is an additional effect of domiphen, but this effect cannot be observed at days 9 and 14.

FIG. 9 summarises the result of 3 experiments obtained with 12 rats as control, 17 rats with treatment with 2% mcz, 8 rats with domiphen bromide only, 18 rats with treatment with 2% MCZ+⅓ DB, 6 rats with treatment with 2% MCZ+⅙ DB.

Example 9 Potentiation of Miconazole by Domiphen Bromide Against *Candida glabrata* Biofilms Materials and Methods Strains and chemicals. *C. glabrata* strain BG2 was grown on YPD (1% yeast extract, 2% bacteriological peptone (LabM, UK) and 2% glucose (Sigma-Aldrich, USA)) agar plates at 30° C. Stock solutions of miconazole (MCZ) (Sigma-Aldrich) were prepared in DMSO (VWR International, Belgium). RPMI 1640 medium (pH 7.0) with L-glutamine and without sodium bicarbonate was purchased from Sigma-Aldrich and buffered with MOPS (Sigma-Aldrich). Domiphen bromide (DB) was supplied by Purna Pharmaceuticals and a work solution of 1% triton (Sigma-Aldrich) was prepared in phosphate buffered saline (PBS).

Biofilm checkerboard assay with CFU determination. A *C. glabrata* BG2 overnight culture, grown in YPD at 30° C., was diluted to an optical density of 0.1 (approximately $10^6$ cells/mL) in RPMI medium and 100 μl of this suspension was added to the wells of a round bottomed microplate (TPP Techno Plastic Products AG, Switzerland). After 1 h of adhesion at 37° C., the medium was aspirated and biofilms were washed with 100 μL PBS to remove non-adherent cells, followed by the addition of 100 μL RPMI 1640 medium. Biofilms were allowed to grow for 24 h at 37° C. To determine possible potentiation of MCZ by DB, a checkerboard assay was used. A combination of MCZ and DB, two fold diluted across rows and columns of a microplate respectively, was added to *C. glabrata* biofilms (DMSO background 1%). After 38 h of incubation at 37° C., CFU determination was performed on treated biofilms. To this end, biofilms were washed with PBS, thoroughly scraped off the bottom of the plate and dissolved in 100 μl triton (1%). Serial dilutions ($10^{-2}$, $10^{-3}$ and $10^{-4}$) were plated on YPD agar plates, followed by an incubation period of 24 h at 37° C. and subsequent colony counting.

Results and Discussion

Domiphen Bromide Potentiates Miconazole Against *C. albicans* Biofilms

Quaternary ammonium compounds, like DB, are potentiators of MCZ against *C. albicans* biofilms. In order to determine whether DB is also a potentiator of MCZ against *C. glabrata* biofilms, a checkerboard experiment was performed FIG. 10 shows the Survival of *C. glabrata* biofilm cells after single -or combination treatment with MCZ and DB. Mean log CFU values +/−SEM are shown for 6 biological repeats. Statistical analysis was performed to assess significant differences between both single treatments with MCZ (150 μM) and DB (37,5 μM) and a combination. A 2-way ANOVA and Tukey multiple comparisons test were performed and significant differences are shown.

Concentration series of both compounds were tested and a significant reduction in CFUs was only observed for a combination of 500 μM MCZ with 37,5 μM DB as compared to single compound treatment.

The Observed Potentiation of MCZ by DB Appears to be MCZ-specific

We assessed whether DB could also increase the activity of posaconazole against *C. glabrata* biofilms. Posaconazole showed no significant antibiofilm activity on its own nor in combination with DB (data not shown).

Example 10 Potentiation of Azoles by Domiphen Bromide Against *Candida albicans* Biofilms Strains and chemicals. Both *C. albicans* strain SC5314 and strain B59630, kindly supplied by the laboratory of Microbiology, Parasitology and Hygiene from prof. Paul Cos, were grown on YPD (1% yeast extract, 2% bacteriological peptone (LabM, UK) and 2% glucose (Sigma-Aldrich, USA)) agar plates at 30° C. Stock solutions of miconazole (MCZ) (Sigma-Aldrich), ketoconazole (TCI Europe, Belgium), clotrimazole (Sigma-Aldrich), itraconazole (TCI) and fluconazole (MP Biomedicals, France) were prepared in DMSO (VWR International, Belgium). Posaconazole (Noxafil) was bought from MSD. RPMI 1640 medium (pH 7.0) with L-glutamine and without sodium bicarbonate was purchased from Sigma-Aldrich and buffered with MOPS (Sigma-Aldrich). Domiphen bromide (DB) was supplied by Purna Pharmaceuticals and a work solution of 1% triton (Sigma-Aldrich) was prepared in phosphate buffered saline (PBS).

Biofilm checkerboard assay with CFU determination. A *C. albicans* overnight culture, grown in YPD at 30° C., was diluted to an optical density of 0.1 (approximately $10^6$ cells/mL) in RPMI medium and 100 μl of this suspension was added to the wells of a round bottomed microplate (TPP Techno Plastic Products AG, Switzerland). After 1 h of adhesion at 37° C., the medium was aspirated and biofilms were washed with 100 μL PBS to remove non-adherent cells, followed by the addition of 100 μL RPMI 1640 medium. Biofilms were allowed to grow for 24 h at 37° C. To determine possible potentiation of the antifungal agents by DB, checkerboard assays were used. A combination of the antifungal compound, either an imidazole (MCZ, ketoconazole or clotrimazole) or a triazole (fluconazole, itraconazole or posaconazole), and DB, two fold diluted across rows and columns of a microplate respectively, was added to *C. albicans* biofilms. After 24 h of incubation at 37° C., CFU determination was performed on treated biofilms. To this end, biofilms were washed with PBS, thoroughly scraped off the bottom of the plate and dissolved in 100 μl triton (1%). Serial dilutions ($10^{-1}$, $10^{-2}$ and $10^{-3}$) were plated on YPD agar plates, followed by an incubation period of 24 h at 37° C. and subsequent colony counting.

Results and Discussion

Quaternary ammonium compounds, like DB, are potentiators of MCZ against *C. albicans* biofilms. Imidazoles, for example MCZ, and triazoles, like fluconazole, are two groups of azoles, characterized by 2-and 3 nitrogen atoms in the azole ring respectively (Cleary et al. (1990). DICP, *Annals of Pharmacother.*, 24: 148-152; Troyer et al. (2013). *J.chem.*, 2013: 1-23). Azoles inhibit ergosterol biosynthesis and miconazole has an additional effect on the cell's mitochondria (Cleary et al. (1990). DICP, *Annals of Pharmacother.*, 24: 148-152; Ghannoum & Rice (1999). *Clinical microbial. reviews*, 12(4): 501-517; Portillo & Gancedo (1984) *Eur. J Biochem*, 143(2): 273-276; Swamy et al. (1974). *Antimicrob. Agents Chemother.* 5(4): 420-425). In order to determine whether DB also potentiates other imidazoles and triazoles against *C. albicans* biofilms, checkerboard experiments were performed (FIG. 11).

FIG. 11 shows survival of *C. albicans* biofilm cells after single -or combination treatment with an antimycotic and DB. (panels A-D) Survival of *C. albicans* strain B59630 or strain SC5314 biofilm cells after single -or combination treatment with an imidazole and DB. Mean log CFU values +/−SEM are shown for at least 3 biological replicates. Statistical analysis was performed to assess significant differences between both single treatments with DB and with either miconazole (A and C) (150 μM), ketoconazole (panel B) (300 μM) or clotrimazole (panel D) (150 μM) and combinations (DMSO background 1%). A 2-way ANOVA and a Tukey multiple comparisons test were performed and significant differences are shown.

(E-G) Survival of *C. albicans* SC5314 biofilm cells after single -or combination treatments with a triazole and DB. Mean log CFU values +/−SEM are shown for at least 2 biological replicates. Statistical analysis was performed to assess significant differences between both single treatments with DB and with either fluconazole (panel E) (150 µM), itraconazole (panel F) (75 µM) or posaconazole (panel G) (285 µM) and combinations (DMSO background 1%, 2% and 0,5% respectively). A 2-way ANOVA and a Tukey multiple comparisons test were performed and P-values are shown.

Concentration series of both the azole and DB were tested and the combination, resulting in the most significant CFU reduction, is shown in FIG. 11. Significant reductions in CFUs were only observed for combinations of DB with imidazoles as compared to single compound treatments. The combination MCZ and DB resulted in significant reductions in CFUs as compared to single compound treatments for both *C. albicans* strain SC5314 and strain B59630. In a few cases, treatment with these combinations resulted in complete sterility of the surface. Triazoles showed no significant antibiofilm activity on their own nor in combination with DB, indicating that the observed potentiation of imidazoles by DB is imidazole-specific.

Example 11. Potentiation of Miconazole by Domiphen Bromide Against *C. glabrata* Biofilms Materials and Methods Strains and chemicals. *C. glabrata* strain BG2 was grown on YPD (1% yeast extract, 2% bacteriological peptone (LabM, UK) and 2% glucose (Sigma-Aldrich, USA)) agar plates at 30° C. Stock solutions of miconazole (MCZ) (Sigma-Aldrich) were prepared in DMSO. RPMI 1640 medium (pH 7.0) with L-glutamine and without sodium bicarbonate was purchased from Sigma-Aldrich and buffered with MOPS (Sigma-Aldrich). Domiphen bromide (DB) was supplied by Purna Pharmaceuticals.

Checkerboard assay with determination of the minimal inhibitory concentration (MIC). A *C. glabrata* BG2 overnight culture, grown in YPD, was diluted to an optical density of 0.1 (approximately $10^6$ cells/mL) in RPMI medium, preheated at 37° C. 90 µL of the cell suspension was added to the wells of a 96 well plate, containing 10 µL of a combination of MCZ and DB, two fold diluted across rows and columns respectively (DMSO background 2%). After both 24 h and 48 h of incubation at 37° C., absorbance was measured at 490 nm by a multimode reader (Synergy Mx multi-mode microplate reader, BioTek, USA).

Miconazole is Potentiated by DB Against Planktonic *C. glabrata* Cultures

Domiphen bromide (DB) is a potentiator of miconazole against *C. glabrata* biofilms. To determine whether DB also potentiates miconazole against planktonic *C. glabrata* cultures, the minimal inhibitory concentration (MIC), the miconazole concentration leading to a reduction in visible growth of 50%, was determined by means of a checkerboard assay (FIG. 12). MIC values were determined using Graphpad Prism 6 (table 8).

FIG. 12 shows that combined MCZ-DB treatment reduces the MIC value as compared to mono treatment of MCZ against *C. glabrata* planktonic cultures. The values represent the mean visible growth of 3 biological repeats (A) as a percentage of the control treatment (2% DMSO) and (B) as a percentage of mono treatment with corresponding DB concentration. For different DB concentrations, dose-response curves of miconazole are shown in different colors (0 µM blue; 0,78 µM red; 1,56 µM green and 3,125 µM purple). A concentration series of MCZ, ranging from 0,0075 µM to 1 mM was tested. Absorbance was measured after 24 h of treatment.

TABLE 8

MIC values for 24 h treatment with MCZ-DB combination against planktonic *C. glabrata* cultures.

| [DB] (µM) | 0 | 0.78 | 1.56 | 3.125 |
|---|---|---|---|---|
| MIC value (µM) | | | | |
| MCZ + DB (24 h) | 6.772277 | 7.227962 | 6.815345 | 0.1943 (# #) |

MIC values, significantly reduced as compared to the mono treatment with MCZ, are indicated in green by # #.

Graphpad Prism 6 was used to calculate MIC values.

The checkerboard data show that, in the presence of DB, significantly lower concentrations of MCZ can be used to reduce visible growth with 50% as compared to mono treatment with miconazole. A significant reduction of the MIC value was observed for 3,125 µM DB.

Furthermore, benzalkonium chloride (BKC), another quaternary ammonium compound, could not potentiate MCZ against planktonic *C. glabrata* cultures (See FIG. 12C).

The invention claimed is:

1. A method for treating or preventing a fungal infection in an animal in need thereof, the method comprising topically administering an effective amount of a composition comprising an imidazole or a salt thereof, and domiphen bromide as active ingredients wherein said imidazole is chosen from ketoconazole and clotrimazole and the fungal infection is a biofilm.

2. The method according to claim 1, wherein the biofilm fungal infection is an infection with *Candida sp.*

3. The method according to claim 1, wherein the biofilm fungal infection is an infection with *Candida albicans*.

4. The method according to claim 1, wherein the biofilm fungal infection is a vulvovaginal infection.

5. The method according to claim 1, wherein the biofilm fungal infection is recurrent vulvovaginal candidiasis.

6. The method according to claim 1, wherein said imidazole or salt thereof and said domiphen bromide are present in a synergistically effective concentration.

7. The method according to claim 1, wherein said imidazole or salt thereof is present in a molar excess of 6 over domiphen bromide.

* * * * *